United States Patent [19]
Keung

[11] Patent Number: 5,610,064
[45] Date of Patent: Mar. 11, 1997

[54] BACTERIUM USEFUL IN THE REMOVAL OF SULPHUR BLACK DYE FROM A SUBSTRATE

[76] Inventor: Mark K. Keung, Dept. of Biology/Chinese University of Hong Kong, Shatin NT, Hong Kong

[21] Appl. No.: 198,044

[22] Filed: Feb. 16, 1994

[51] Int. Cl.$^6$ .................................................. D06M 16/00
[52] U.S. Cl. .......................................... 435/262; 435/264
[58] Field of Search .............................. 435/262, 262.5, 435/832, 859, 264; 548/457; 8/461

[56] References Cited

FOREIGN PATENT DOCUMENTS 1592330  9/1990  U.S.S.R. .

OTHER PUBLICATIONS

Bujak H., Effectiveness of Biochemical . . . Przegl Wlok (1979) 33 (4) 214–217.
Women's Wear Daily, Biodegradable Process for Indigo . . . Jun. 4, 1991, p. 10.
Mou, D., Microbial Agents for Decolorization of Dye . . . Biotech Adv 9: 613–622 (1991).
Bujak, H., Effectiveness of Biochemical . . . Przegl Wlok (1979) 33 (4) 214–217 English Translation.
Dohányos et al., "Removal of Organic Dyes by Activated Sludge", *Prog. Wat. Tech.* 10(5/6):559–575 (1978).
Hitz et al., "Publication Sponsored by ETAD The Adsorption of Dyes on Activated Sludge", *J. Soc. of Deyers & Colorists* pp. 71–76 Feb. 1978.

Mou et al., "Microbial Agents for Decolorization of Dye Wastewater", *Biotech. Adv.* 9:613–622 (1991).
Mullen et al., "Bacterial Sorption of Heavy Metals", *Applied and Environmental Microbiology* 55(12):3143–3149 (1989).
Pagga and Brown, "The Degradation of Dyestuffs: Part II Behavior of Dyestuffs in Aerobic Biodegradation Tests" *Chemosphere* 15(4):479–491 (1986).
Wan, "Discovery to Attack Dye Pollution", *South China Sunday Morning Post*, Hong Kong, Sunday, Jun. 10, 1990.
"Biodegradable Process for Indigo Dyeing Claimed in Hong Kong", *Womens Wear Daily*, (Jun. 4, 1991) p. 10.
"New Biodegration Technology for Textile Dyes Developed", *Southern Textile News* 47(29):6 (1991).
Gwynne, "Pollution Eaters", *Far Eastern Economic Review* (Jul. 11, 1991) p. 58.
Gwynne, "Biotech Grows in Hong Kong", *Nature* 352:273 (1991).

*Primary Examiner*—Ralph J. Gitomer
*Attorney, Agent, or Firm*—Bertram I. Rowland; Bret E. Field; Flehr, Hohbach, Test

[57] ABSTRACT

Bacteria capable of reducing the concentration of sulphur black dye in a substrate when contacted with the substrate are provided. The subject bacteria may be either aerobic or anaerobic and reduce the concentration of sulphur black dye in the substrate through either bioadsorption or biodegradation of sulphur black dye.

2 Claims, 9 Drawing Sheets

Figure 9. Growth curves of bacterial strain L5 (viable cell count)

5,610,064

BACTERIUM USEFUL IN THE REMOVAL OF SULPHUR BLACK DYE FROM A SUBSTRATE

TECHNICAL FIELD

The field of this invention is bioremoval of sulphur black dye from a substrate.

BACKGROUND

Sulphur black is a popular black dye. Because it is very stable and does not fade, even under strong sunlight, it has become a major dyestuff, particularly used for the manufacture of black denim and similar cotton textiles. It is estimated that annual production of sulphur black dye is about 12,000 tons per year. Use of sulphur black dye is prominent in third world and developing nations because it is cheap and particularly suited for cotton textile production, e.g. black denim jeans.

Sulphur black dye is produced by heating 2,4-dinitrophenol with sodium polysulfide at elevated temperatures under pressure. The resultant "melt" may then be diluted with water and air blown to oxidize the reduced form to an insoluble dye. During air blowing, sodium thiosulfate is formed and remains in the mother liquor. A proposed structure for sulphur black dye involves a substituted dibenzthiazine. For the most part, sulphur black is water insoluble, but can be solubilized by various treatments.

While sodium thiosulfate finds extensive commercial use, it cannot be recovered from the mother liquor of the sulphur black formation process because significant amounts of sulphur black are retained in the mother liquor. Furthermore, when using sulphur black, the spent solutions used for dying require disposal. Since sulphur black is very dark and imparts a dark color to the aqueous medium in which it is present, dumping of sulphur black into bodies of water is undesirable. Unfortunately, sulphur black dye does not seem to be readily degraded or removed from these aqueous mediums by conventional sewage treatments.

In addition, the textile industry is often interested in removing a portion of the sulphur black dye present in recently dyed substrates, e.g. in the production of "stonewashed" clothing. Traditional methods for removing dye from substrates make use of bleaching reagents, such as hypochlorite. However, hypochlorite and similar bleaching reagents are considered by many governmental agencies to be harmful to the environment. Accordingly, many governmental agencies have either prohibited, or at least heavily regulated, their use.

Accordingly, there is substantial interest in finding ways to treat solutions which comprise unwanted sulphur black dye. For example, there is interest in finding ways to remove sulphur black dye from the sulphur black mother liquor so that the sodium thiosulfate can be recovered for further commercial application. There is also substantial interest in finding ways to treat the waste streams produced by textile dyeing facilities so as to remove and degrade unwanted sulphur black dye. Further, there is substantial interest in finding new ways to remove sulphur black from dyed substrates.

Relevant Literature

Bioremediation has been taught for a number of organisms in association with heavy metals in Mullen et al., Applied & Environmental Microbiology (1989) 55: 3143–3149. Hitz et al., J. Soc. of Dyers & Colorists (1978) February: 71–76, studied the adsorption of dyes on activated sludge. See also Dohanyos, Progress in Water Technology (1978) 10:559–575. Pagga and Brown, Chemosphere (1986) 15:479–491 demonstrated the inadequacy of anaerobic biodegradation in short-term anaerobic tests. Mou et al., Biotech. Adv. (1991) 9:613–622 reported non-specific adsorption of various dyes using microbial agents.

SUMMARY OF THE INVENTION

Sulphur black dye is removed from substrates, particularly liquids, through bioremoval. The microorganisms employed in the bioremoval process are capable of bioadsorption and/or biodegradation of the sulphur black dyes. Of particular interest are bacteria capable of efficient bioadsorption of sulphur black dye or biodegradation of sulphur black dye.

DESCRIPTION OF SPECIFIC EMBODIMENTS

Figure 1:
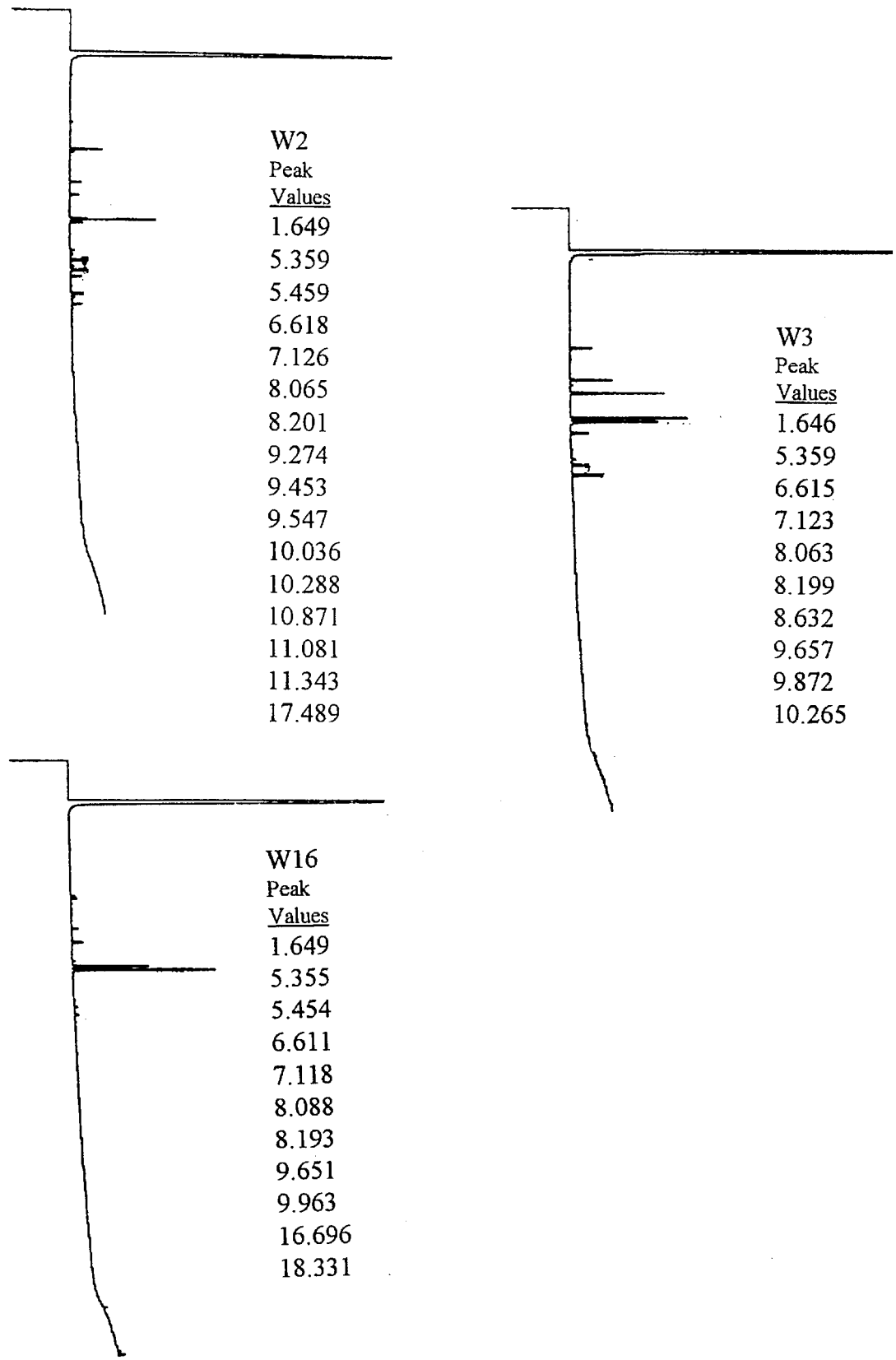
FIG. 1 is a representation of the fatty acid profile for strains W2, W3 and W16.

Methods and cellular compositions are provided for the bioremoval of sulphur black dye from substrates, including liquids, solids and the like of particular interest are waste streams associated with the production of sulphur black dye and waste streams produced by textile dyeing manufacturers. Bioremoval of sulphur black from substrates is accomplished by microorganisms through the processes of bioadsorption or biodegradation.

Bioremoval as used in the subject invention refers to the reduction in the concentration of sulphur black dye in substrates by microorganisms which are capable of one or both of the following processes: bioadsorption and biodegradation. In describing the subject invention, the bioadsorption component of the subject invention will be discussed first. Following that, the biodegradation component of the subject invention will be described.

Bioadsorption, as used here, refers to the uptake of sulphur black dye molecules by a microorganism from the ambient medium of the microorganism. Though not wishing to be limited to a particular theory, one possible mechanism by which bioadsorption is accomplished by the microorganisms of the subject invention is the adsorption of the dye molecules from the ambient solution of the microorganism onto the cell surface.

A variety of microorganisms may find use in bioadsorption. These microorganisms may include bacteria, fungi and the like. The microorganisms which find use in the subject invention may be screened using any convenient means. The following process is exemplary of a suitable screening process. A sulphur black dye containing rich growth medium is prepared, e.g. IM medium. The sulphur black dye which is commercially available as a powder or in solution (referred to as Sodyesul Black), can be dissolved in the medium. After sterilizing the sulphur black dye containing IM medium, the medium is inoculated with a candidate cell population, incubated at 37° C. and any change in color observed. Alternatively, one may prepare the sulphur black dye containing media, where the media is combined with agar and the candidate cell population. This sulphur black agar containing media inoculated with the candidate cell population is then poured onto solidified agar containing medium lacking the sulphur black dye. Change in color is then monitored, where the formation of a lightly shaded ring or halo in the otherwise dark background is indicative of the location of a bioadsorprtion strain. Bioadsorption candidate cell populations are obtained from any convenient source, e.g. sulphur black dye polluted waters.

The microorganisms of interest in the bioadsorption component of the subject invention are those shown to be able to strongly adsorb sulphur black dye so as to substantially accumulate the sulphur black dye with the cells, leaving the substrate being treated substantially free of the sulphur black dye, particularly free of the dark coloration associated with the dye.

These microorganisms have the following general characteristics. They are gram positive rods and cocci. They are facultatively aerobic and can absorb sulphur black dye from a solution. They grow aerobically on an IM agar plate at 37° C. They are classified in the families Bacillaceae and Micrococcaceae. Bacterial strains which are useful in the bioadsorption component of the subject invention include the bacterial strains referred to as W2, W3, W11 and W16.

Strains W2, W3 and W16 display the characteristic fatty acid profiles shown in FIG. 1 as determined using the methodology of Microcheck, Inc. (Microcheck, Inc., P.O. Box 456, 48 South Main Street, Northfield, Vt 05663). W3 has a similarity index, as determined by Microcheck, Inc., of 0.074 with *Bacillus cirulans* GC subgroup B and an ATCC number of 55566, deposited on May 3, 1994. W2 has a similarity index of 0.414 with *Bacillus mycoides* GC subgroup A. W16 has a similarity index of 0.297 with *Micrococcus lylae* GC subgroup A.

W3 is further characterized by the following features. W3 is aerobic and achieves an optimal growth rate at a pH of 7. W3 is gram positive, and upon staining with crystal violet or safranin, appears as a short, rod-like shape. W3 grows at pH values ranging from 6 to 10, generally 6–9, and preferably at a pH value of 7. W3 grows at temperatures ranging from 20° to 48° C., preferably at 37° C. W3 displays tolerance to NaCl concentrations up to and including 5% concentration. W3 metabolizes glucose, xylose and arabinose. W3 utilizes nitrate.

Bioremoval of sulphur black from substrates through use of bioadsorption microorganisms generally involves contacting the substrate with the microorganism for a sufficient time to reduce the concentration of sulphur black present in the substrate. The conditions for bioadsorption will be selected to substantially optimize the amount and rate at which sulphur black dye is removed from the substrate. The time for treatment will vary greatly, depending upon the amount and concentration of the sulphur black dye in the substrate, the other constituents in the medium, the temperature, pH, and the efficiency with which the particular cell strain adsorbs the sulphur black dye. Thus, treatment may vary from passing through a column for a period of minutes to batch treatment, filter percolation, activated sludge treatment into which the subject strain is inoculated, or the like.

The total amount of cells used in the bioremoval process will depend on the particular treatment employed. The bioadsorption microorganisms of the subject invention can be grown in any appropriate growth medium, depending on the total cell population required for a particular medium, preferably a rich medium such as IM medium. In growing the cells, the cells may be grown for a time period of 0–30 hours, preferably 5–20 hours, more preferably 5–15 hours. In growing the cells, the cells may be incubated at temperatures ranging from about 20° to 48° C., preferably at 37° C.

It appears that the presence of sodium thiosulfate augments the removal of the sulphur black dye by bioadsorption strains. Therefore, when appropriate, in the absence of sodium thiosulfate, small amounts of a thiosulfate may be added to the medium, generally at a concentration in the range of from about 0.05 to 1.0M, preferably about 0.05 to 0.2M.

The cell dosage will vary widely, where the dry weight of the cells may vary from about 10 to 1000 times the weight of sulphur black dye in the medium, more usually being at least about 10 to 100 times the weight of sulphur black dye present in the medium to be treated.

The pH will generally be in the range of about 6 to 12, preferably about 6 to 9. The temperature will generally be in the range of about 10°–60° C., preferably in the range of about 20°–40° C.

Mechanical agitation may be employed and the medium may be aerated to support the maintenance of the cells. For the most part, nutrients will not be added to the medium, rather, the cells will be substantially non-proliferating during the treatment, although if desired, sufficient nutrients may be added to allow for cell proliferation.

The cells, whether alive or dead, provide for strong adsorption of sulphur black dye. Thus, the cells, or fragments thereof, may be used for adsorption of sulphur black dye, without concomitant biodegradation or with biodegradation, depending upon the particular need. For example, one may wish to reduce the total concentration of sulphur black dye in a waste source. In a first step one may use the cellular composition to adsorb a significant proportion of the total amount of sulphur black dye present. This first step may be followed by a bioadsorption and biodegradation second step, which may require a greater time period.

Substrates suitable for bioremoval treatment through contact with bioadsorption microorganisms include any substrate in which one desires to reduce the concentration of sulphur black dye. Substrates of interest include processing waste streams, textile dyeing waste streams and the like. For example, bioadsorption microorganism are useful in treating sulphur black processing streams. By contacting the waste stream with a suitable amount of bioadsorption cells, the concentration of sulphur black dye in the waste stream is reduced to a level where sodium thiosulfate can be isolated. Further, the subject cells can be used to remove sulphur black molecules from the waste streams of textile dyeing facilities before disposal of these streams into conventional sewage treatment streams.

Bioremoval of sulphur black dye from a substrate may also be accomplished through biodegradation of the sulphur black dye molecules. Biodegradation, as used here, refers to the process of converting sulphur black dye molecules to acceptable products, e.g. non-chromogenic and non-toxic. As with bioadsorption, microorganisms that are suitable for biodegradation include bacteria, fungi and the like.

Isolation of microorganisms that display biodegradation activity may be accomplished by any convenient means, e.g. the process described previously for the isolation of bioadsorption microorganisms. In order to confirm that the bioremediation is resulting from a biodegradation activity of the microorganisms, and not a bioadsorption activity, a second test may be employed. A second test which may be employed is the test commonly referred to as the top agar plate method (TAP) and is described in detail in the working exemplification section.

Generally, microorganisms suitable for biodegradation may be aerobic and are facultatively anaerobic. They are gram-positive rods or cocci classified in the families Micrococcaceae and Streptococcaceae. They grow in IM medium at 37° C. and degrade sulphur black dye.

Figure 2:
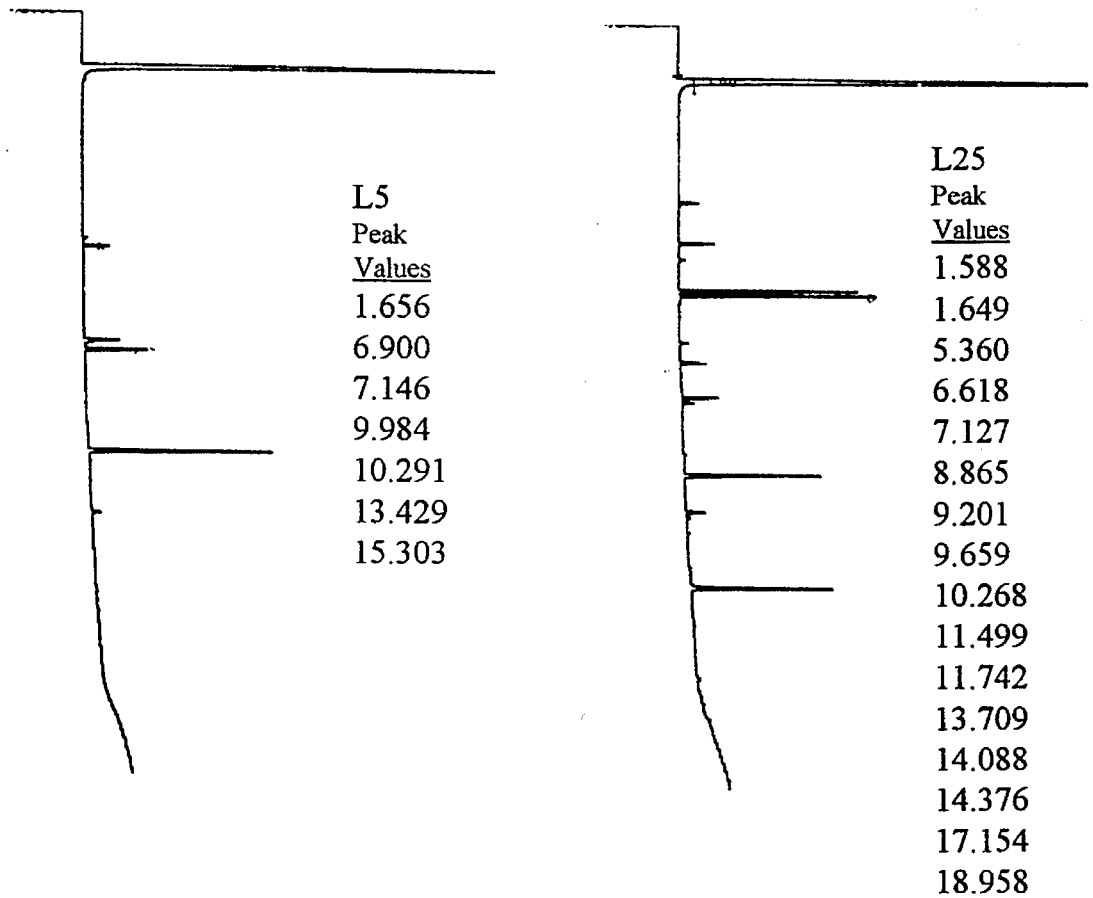
FIG. 2 is a representation of the fatty acid profile for strains L5 and L25.

Bacterial strains that display the above characteristics and are suitable for biodegradation include the strain designated L5 and the strain designated L25. L5 and L25 exhibit characteristic fatty acid profiles shown in FIG. 2 as determined by Microcheck. L25 has a Microcheck similarity index of 0.292 with *Staphylococcus haemolyticus* L5 has a Microcheck similarity index with *Enteroccocus durans* of 0.528. L5 has an ATCC number of 55565, deposited on May 3, 1994.

L5 has been further characterized as follows: biodegrades sulphur black dye; is a gram positive cocci; facultatively anaerobic; lacks oxidase activity; ferments glucose, arabinose and xylose to produce acid and gas; ferments lactose, maltose, sucrose and mannitol to produce gas only; has catalase activity; reduces nitrate to nitrite; IMV C= . . . +; produces hydrogen sulfide from sulphate; hydrolysis starch, tributyrin and casein, but not gelatin; reduces litmus; possesses rennin-like and pepsin-like enzymes; and is resistant to the antibiotics ampicillin, bacitracin, neomycin, penicillin G, polymyxin B, rifampin, streptomycin, tetracycline and oxytetracycline, but is only moderately resistant to nalidixic acid.

Cells capable of biodegradation can be used for bioremoval in substantially the same manner as bioadsorption cells are used, as described above. The substrate to be treated is generally contacted with the biodegradation cells for a sufficient time to reduce the concentration of the sulphur black in the substrate. However, unlike cells used for bioadsorption, depending on the particular protocol the cells used in biodegradation may not have to be harvested following treatment of the substrate. Thus, biodegradation cells can be used in place of traditional substrate bleaching reagents, e.g. hypochlorite. Further, the subject cells can be used in place of pumice stones or cellulase that are traditionally used in the "stone-wash" process of the textile industry.

The subject microorganisms of interest may be modified in a variety of ways, so as to change their growth characteristics, enhance their sulphur black dye degrading capabilities, improve their growth characteristics and the like. Thus, genes from other strains may be isolated and screened for improving one or more traits of the subject strain of interest. Alternatively, the subject strain may be randomly mutagenized using conventional mild techniques, such as x-ray irradiation, mutagens, such as alkylating agents, cross-linking intercalating agents, such as psoralen, nitrogen mustards, or the like. These mutagenizing agents have found extensive use and do not require description here. The conditions are selected to minimize the number of mutations to a few, usually at an efficiency of at least about 1 per $10^2$ cells. The mutagenized cell lines may then be screened as described above for their ability to degrade sulphur black.

It is also contemplated that the gene or the portion of the gene relevant to sulphur black dye degradation derived from the sulphur black dye degradation microorganisms mentioned above can be isolated and cloned into other organisms for such applications. The isolation and identification of the gene can be performed by sequencing the enzyme to determine the amino acid sequence. Various commercially available sequencers may be used. From the amino acid sequence probes may be prepared with the appropriate redundancy for the codons encoding the selected sequence. Usually the probe will be at least 12 nucleotides, preferably at least 16 nucleotides, and not more than about 40 nucleotides and will be a mixture providing for the codon degeneracy encoding the individual amino acids. The degree of redundancy may be diminished by allowing for the codon preference of the organism from which the enzyme was obtained. A genomic DNA library is prepared according to known methods, usually inserting restriction fragments of at least about 0.5 knt into a cloning vector. See, for example, Sambrook et al., Molecular Cloning: A Laboratory Manual, CSHL, Cold Spring Harbor, N.Y., 1989.

The DNA library is screened with the probes employing Southern hybridization, and hybridizing DNA isolated, conveniently inserted into a convenient expression vector, either plasmid or phage, and the vector transformed into an expression host having a negative background for sulphur black dye degradation. Where the host having a negative background for the sulphur black dye degradation is a different species from the source of the DNA, it may be desirable to provide for different transcriptional regulatory sequences native to the expression host. One can create a negative host, by lightly mutagenizing the sulphur black degrading host and screening for a loss of sulphur black degradation capability. The transformants are then expanded and assayed for sulphur black degradation. Positive clones may then be harvested, the DNA isolated and characterized, e.g. sequenced, and the DNA used for expression of the enzyme. The DNA may be used as a probe with the DNA library to determine whether the entire gene has been isolated.

If desired, an expression cassette may be prepared, where the natural promoter is substituted with a more active promoter. A wide variety of strong bacterial promoters are available, particularly from bacteriophage genes, such as T7, λ, and the like. The expression cassette may be introduced into the expression host as a plasmid or linear DNA for integration. The expression host is then grown in an appropriate nutrient medium, the cells separated from the medium and the enzyme isolated from the nutrient medium, as described previously.

Any convenient bacterial host may be employed, depending upon the use of the sulphur black degrading host. Thus, one need not be restricted to the native host, but may use more convenient hosts for use as organisms for sulphur black degradation or for use for the production of the enzyme. Conveniently, *E. coli* or other well characterized and acceptable organisms may be employed as the expression host.

Instead of using whole cells to degrade the sulphur black dye, one may employ the enzymes present in the subject cells. The biodegradation enzymes of the subject invention find use in any substrate in which it is desired to reduce the concentration of sulphur black dye. Further, the biodegradation enzymes are suitable for the treatment of textile substrates, e.g. enzyme washing. For use in sulphur black degradation, the enzyme may be isolated from the native host or produced recombinantly. A crude mixture, e.g. lysate, containing the enzyme may be employed, where the enzyme is at least about 1 weight % of total protein or an enriched mixture may be employed, where the enzyme is at least 10 weight % of total protein, preferably at least 25 weight % of total protein. Of course, if desired, the enzyme may be isolated and purified by conventional techniques, e.g. HPLC, solvent extraction, affinity purification, etc., to at least 50 weight %, usually at least 90 weight %, or substantially total purity.

The following examples are offered by way of illustration and not by way of limitation.

EXPERIMENTAL

I. Isolation, Characterization and Activity of Bioadsorption Bacterial Strains, Including W3.
A. Materials and Solutions
 1. Materials Sulphur black dye (water soluble) was obtained from Chek Tak dyeing factory Ltd. Sodium thiosulfate ($Na_2S_2O_3$) was obtained from Sigma Chemical Company. Potassium iodide (KI) was obtained from Merck. Starch was obtained from Merck. Iodine ($I_2$) was obtained from BDH Chemical Ltd. Tryptone was obtained from Difco Laboratories. Glucose was obtained from BDH Chemical Ltd. Yeast extract was obtained from Difco Laboratories. Ammonium chloride ($NH_4Cl$) was obtained from Merck. Agar was obtained from Sigma Chemical Company. Dibasic sodium phosphate ($Na_2HPO_4.12H_2O$) was obtained from Merck. Monobasic sodium phosphate ($NaH_2PO_4$) was obtained from Merck. Tris-(hydroxymethyl)aminomethane was obtained from Sigma Chemical Company. Sodium hydroxide (NaOH) was obtained from Merck. Potassium chloride (KCl) was obtained from Merck. Potassium dihydrogen phosphate ($KH_2PO_4$) was obtained from Merck. Glycine was obtained from Merck. Hydrochloric acid (HCl) was obtained from Merck. Sodium dodecyl sulfate (SDS) was obtained from Sigma Chemical Company. Triton X-100 was obtained from Sigma Chemical Company. Cetylpyridinium chloride was obtained from CalBioChem. Trypsin was obtained from Merck. Diethyl ether was obtained from Merck. Sodium chloride (NaCl) was obtained from Merck. Activated charcoal was obtained from BDH Chemical Ltd.

2. Solutions

IM medium: 10 g tryptone, 1 g D-glucose, 1 g yeast extract, 1 g $NH_4Cl$ in 1 liter distilled water. IM agar: 15 g agar, 10 g tryptone, 1 g D-glucose, 1 g yeast extract, 1 g $NH_4Cl$ in 1 liter distilled water. Starch solution: 1 g starch in 100 ml boiling water with vigorous stirring. Phosphate buffer: pH 7, 39 ml 0.2M $NaH_2PO_4$, 61 ml 0.2M $Na_2HPO_4.12H_2O$; diluted to 200 ml with $H_2O$. Tris-(hydroxymethyl)aminomethane buffer: pH 9, 50 ml 0.2M tris-(hydroxylmethyl)aminomethane, 5 ml 0.2M HCl; diluted to 200 ml with $H_2O$. Phosphate-NaOH buffer: pH 11, 50 ml 0.5M $Na_2HPO_4$, 4.1 ml 0.1M NaOH; diluted to 100 ml with $H_2O$. Hydroxide-chloride buffer: pH 13, 25 ml 0.2M KCl, 6 ml 0.2M NaOH; diluted to 100 ml with $H_2O$. Potassium dihydrogen phosphate-NaOH buffer: pH 7, 50 ml 0.1 $KH_2PO_4$, 29.1 ml 0.1M NaOH; diluted to 100 ml with $H_2O$.

Glycine-NaOH buffer: pH 9, 25 ml 0.2M glycine, 4.4 ml 0.2M NaOH; diluted to 100 ml with $H_2O$.

B. Screening and Isolation of W3

Water samples polluted by waste from textile dyeing facilities in the South China region were screened for sulphur black dye degrading bacterial strains using the following procedure.

Sulphur black agar plates were formed by first dissolving 0.5 g of sulphur black dye powder into 500 ml of distilled water. The resultant solution was autoclaved and then cooled to 50° C.. The solution was then combined with 500 ml of IM agar solution resulting in a 0.05% sulphur black agar solution. 25–30 ml of the sulphur black agar solution was poured into agar plates.

0.1 ml of the polluted water samples were spread evenly on the sulphur black plates in a manner which formed well separated colonies, e.g. 30–300 colonies per plate. The agar plates were then incubated for 3–4 days at 37° C.

Colonies which were surrounded by a clear halo in the agar medium were chosen as indicative of those colonies capable of bio-adsorption, i.e. could adsorb sulphur black dye. These chosen colonies were then diluted and re-spread on additional sulphur black IM agar plates in order to obtain pure colonies and confirm bioadsorption activity of the selected colonies. Form this process, twenty strains were selected.

Strains from these twenty strains which exhibited the greatest bioadsorption activity were selected using the following procedure. Each strain was cultured in IM medium for one day at 37° C.. Sulphur black dye was then added (approximately 3586 μg/ml) to each culture to obtain an optical density reading of 1.0 at 620 nm (the $OD_{620}$ value). The cultures were then spun in a microfuge 13,000 rpm for 5 min. The following results were obtained.

TABLE 1

| Microbial Strain | OD at 1 min. | OD at 5 min. | OD at 15 min. | OD at 24 hr. | OD at 72 hr. |
|---|---|---|---|---|---|
| W2 | .26 | .25 | .27 | .38 | .75 |
| W3 | .20 | .25 | .16 | .12 | .14 |
| W4 | 1.45 | .96 | 1.03 | .58 | .54 |
| W6 | .77 | .69 | .68 | .45 | .51 |
| W7 | 1.02 | 1.04 | 1.03 | .78 | .74 |
| W8 | 1.01 | 1.03 | 1.02 | .96 | .84 |
| W9 | 1.00 | 1.02 | 1.00 | .93 | .75 |
| W10 | .44 | .41 | .43 | .74 | .69 |
| W11 | .26 | .26 | .23 | .46 | .47 |
| W12 | 1.08 | 1.03 | 1.04 | 1.02 | .83 |
| W13 | .96 | .84 | .90 | .85 | .85 |
| W14 | .56 | .64 | .63 | .59 | .84 |
| W15 | .88 | .89 | .88 | .90 | .90 |
| W16 | .17 | .18 | .20 | .36 | .59 |
| W17 | .92 | .91 | .90 | .88 | .89 |
| W18 | 1.05 | 1.00 | .99 | .96 | .97 |
| W19 | .80 | .78 | .52 | .81 | .33 |
| W20 | .89 | .89 | .91 | .87 | .92 |
| E. Coli | .86 | .84 | .83 | .69 | .79 |
| H12 | .94 | .92 | .95 | .80 | .79 |
| No cells | 1.06 | 1.05 | 1.05 | 1.06 | 1.08 |

As indicated in the above results, strain W3, W2, W11 and W16 displayed significant bioadsorption activity. From these strains, W3 was selected for further characterization and study. W3 was shown to reduce the dark color in the agar method by about one half in one day, by comparing the agar plate with a plate inoculated with *E. coli* and having a 0.3% concentration of sulphur black dye.

C. Characterization of W3

Characterization of the strain W3 by conventional tests provided the following characteristics:

1) Gram positive bacteria (no growth was seen on EMB and tergitol-7 agar plates which are selective for grain negative bacterial);
2) W3 is stainable with crystal violet or safranin and upon staining, appears as a short rod;
3) no endospore is observed;
4) W3 only grows under aerobic conditions;
5) W3 grows best a pH 7, but also at pH 9, but will not grow at pH 3, pH 5 or pH 11;
6) generation time for W3 is 43 min. at pH 7, 37° C.; and
7) W3 can ferment glucose, xylose and arabinose and is capable of nitrate utilization.

D. Further Characterization of the W3 Strain 1. Growth of bacterial strain W3

The cultures were incubated at 37° C. in IM medium and shaken at 200 rpm (Gyrotory Water Bath Shaker, New Brunswick Scientific). Experimental cultures were harvested after 20 hours incubation, then spun down at 10,000 rpm for 10 minutes at 4° C. (High Speed Centrifuge RC5C, Sorvall Instrument). The centrifuged cells were washed with distilled water once.

The growth curve of W3 was constructed by inoculating 1% overnight culture (18 hours) of W3 into a 250 ml conical flask containing 50 ml IM medium. Incubated at 37° C. and shaken at 200 rpm. The cell density of W3 was determined by the plate count method (viable cell count) and by a haemotocytometer (total cell count).

Figure 3:
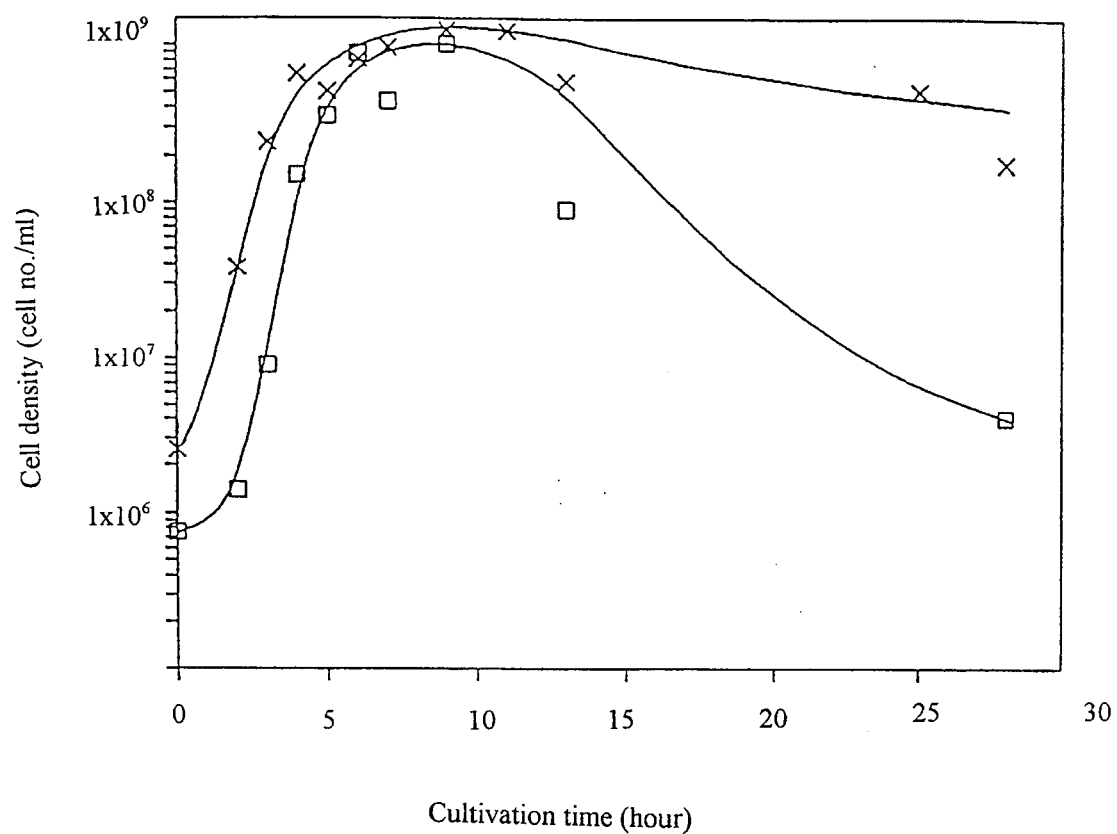
FIG. 3 is a graph representing the growth curve of W3 in IM medium.

A very short lag phase, about 1 to 2 hours, was found in both counting methods. Stationary phase was reached at 7 to 9 hours of cultivation. The cell density in stationary phase was $1 \times 10^9$ cells/ml by viable cell count and $1.25 \times 10^9$ cells/ml total cell count. The culture entered the death phase after 10 hours of cultivation. There was no significant decrease in the total cell density in the death phase. However, a significant decrease of cell density was found in death phase by viable cell count. Viable cells per ml was about $1 \times 10^6$ cells/ml at 24 hours of incubation. See FIG. 3.

2. Standard method for measuring the capacity and efficiency of sulphur black dye removed by W3

Cultures of W3 were centrifuged and washed with distilled water prior to use. The dried weight (oven dry) of 20 ml of an overnight culture of W3 is about 10 mg (equivalent to $2.5 \times 10^{10}$ cells). The washed cell pellet was resuspended in a sulphur black dye solution. After incubation under controlled conditions, the cell-dye mixture was centrifuged at 10,000 rpm for 10 minutes (High Speed Centrifuge RC5C, Sorvall Instrument).

The resultant supernatant was then measured at $A_{625}$ using the Spectronic 601 from Milton Roy. A control was used which did not comprise cells. Based on the standard curve of sulphur black dye, the amount of sulphur black dye removed by W3 was obtained from the change of absorbance of the supernatant using the following formulas:

$$\text{Removal Capacity} = \frac{\text{amount of SB removed (mg)}}{\frac{\text{amount of W3 added}}{\text{(mg in corresponding dry wt.)}}}$$

$$\% \text{ Removal Capacity} = \frac{\text{amount of SB removed (mg)}}{\text{amount of SB added (mg)}} \times 100\%$$

3. Standard Curve of Sulphur Black

A linear relationship was observed between the concentration of sulphur black (range between 0 to 1 mg/ml) and the absorbance at 625 nm. A regression coefficient of r=0.9999 was obtained.

Therefore, the concentration of sulphur black could be calculated from the following equation.

sulphur black (mg/ml)=$(A_{625}-1.79 \times 10^{-3})/17.56$

4. Sulphur Black Dye Removal Efficiency of W3 under Various Conditions a. Effect of medium on sulphur black dye removal The efficiency of sulphur black removal by resting cells of W3 was determined in the following mediums: distilled water, IM medium and 0.1M sodium thiosulfate solution. Resting cells of W3 (10 mg in corresponding dry wt.) were resuspended in 2 ml of medium containing 0.05 mg/ml of sulphur black dye. The cells were then incubated at room temperature for 1 hour. Sulphur black dye removal efficiency was determined using the formula of D.2.

The sulphur black removal efficiency of W3 increased as the medium changed from distilled water to IM medium and to 0.1M sodium thiosulfate. The sulphur black removal efficiency of W3 in 0.1M sodium thiosulfate (about 93%) was much higher than that in distilled water (about 27%). It was concluded that the presence of sodium thiosulfate positively affected the sulphur black uptake by W3.

b. Effect of the amount of cells used on sulphur black dye removal efficiency and capacity The sulphur black removal efficiency and capacity of W3 was determined for the following amounts of W3 cells (in corresponding dry wt.): 1 mg, 10 mg, 50 mg and 100 mg. The various amounts of W3 were resuspended in 2 ml of 0.1M sodium thiosulfate with 0.05 mg/ml of sulphur black dye. The resuspensions were incubated at room temperature for 1 hour. The amount of sulphur black removed by W3 was determined by the standard method of D.2.

Figure 4:
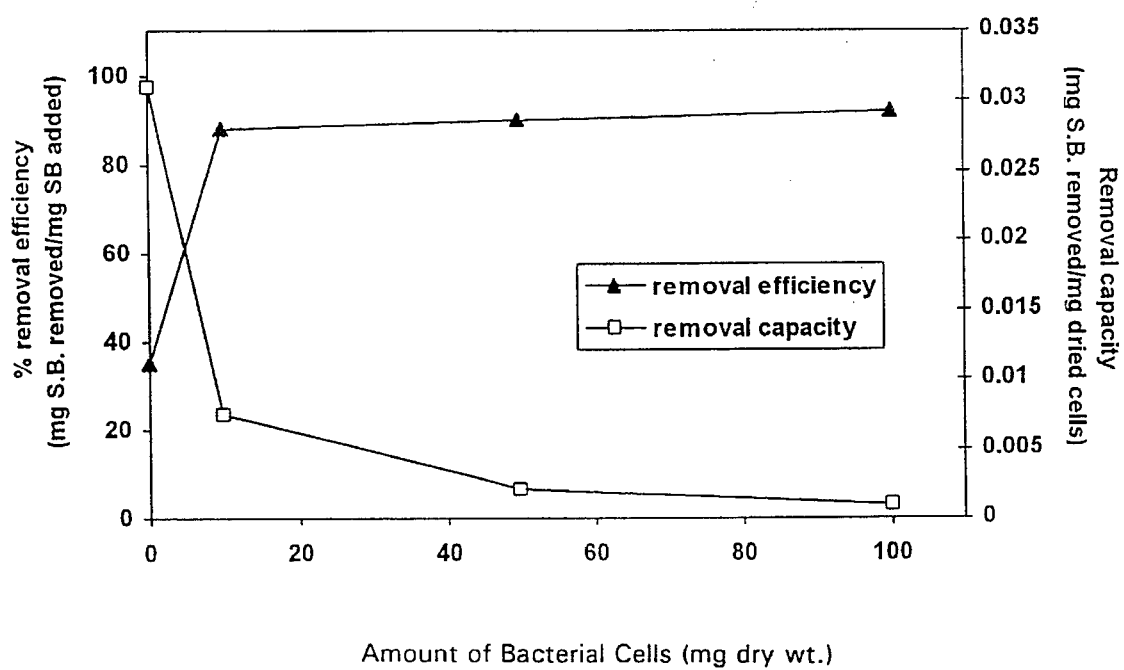
FIG. 4 is a graph indicating the relationship between the amount of cells and the removal of sulphur black dye.

The sulphur black removal efficiency increased with increasing amounts of W3 (from 1 mg to 100 mg of corresponding dry cells). The increase in sulphur black removal efficiency was much sharper upon addition of 10 mg of W3 than upon addition of 1 mg of W3. The rate of increase of sulphur black removal efficiency decreased as the amount of W3 increased from 10 mg to 100 mg. Sulphur black removal capacity decreased with increasing the amounts of applied W3. See FIG. 4.

c. Effect of sulphur black concentration on sulphur black removal efficiency and capacity of W3

10 mg of W3 (in corresponding dry wt.) was resuspended in 2 ml of 0M sodium thiosulfate solution containing various concentrations of sulphur black ranging from 0.01 to 1.0 mg/ml. The resuspensions were incubated at room temperature for 30 minutes. The amount of sulphur black removed by W3 was determined by the standard method of D.2.

Figure 5:
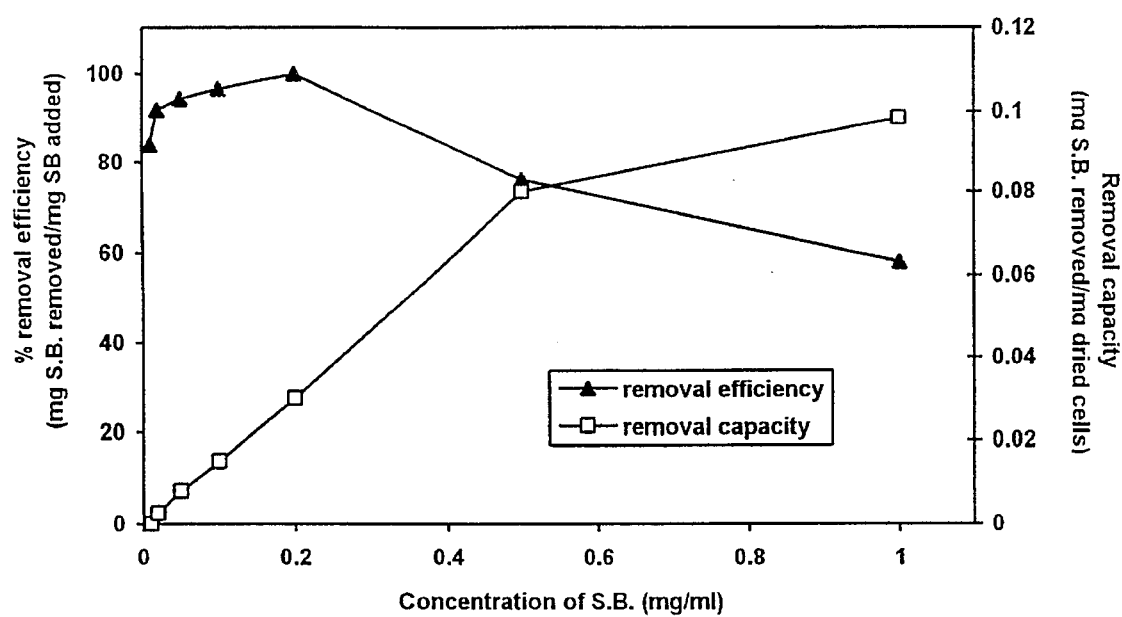
FIG. 5 is a graph of the effect of the concentration of sulphur black dye on the removal capacity and efficiency of resting bacterial cells.

The sulphur black removal capacity of 10 mg of W3 (in corresponding dry wt.) increased gradually as the concentration of sulphur black increased from 0.01 to 0.5 mg/ml. The rate of increase of sulphur black removal capacity slowed as the concentration of sulphur black increased from 0.5 to 1.0 mg/ml. Sulphur black removal efficiency of W3 increased slightly to a maximum (about 99%) when the concentration of sulphur black increased from 0.01 to 0.2 mg/ml and then decreased when the sulphur black concentration rose to 1.0 mg/ml. See FIG. 5.

d. Effect of concentration of sodium thiosulfate on the sulphur black removal efficiency and capacity of W3

10 mg of W3 (in corresponding dry wt.) were resuspended in 2 ml solution with various concentrations of sodium thiosulfate ranging from 0.05 to 1M, and 0.05 mg/ml of sulphur black. The resuspensions were incubated at room temperature for 1 hour. The amount of sulphur black removed by W3 was determined by the standard method of D.2.

Figure 6:
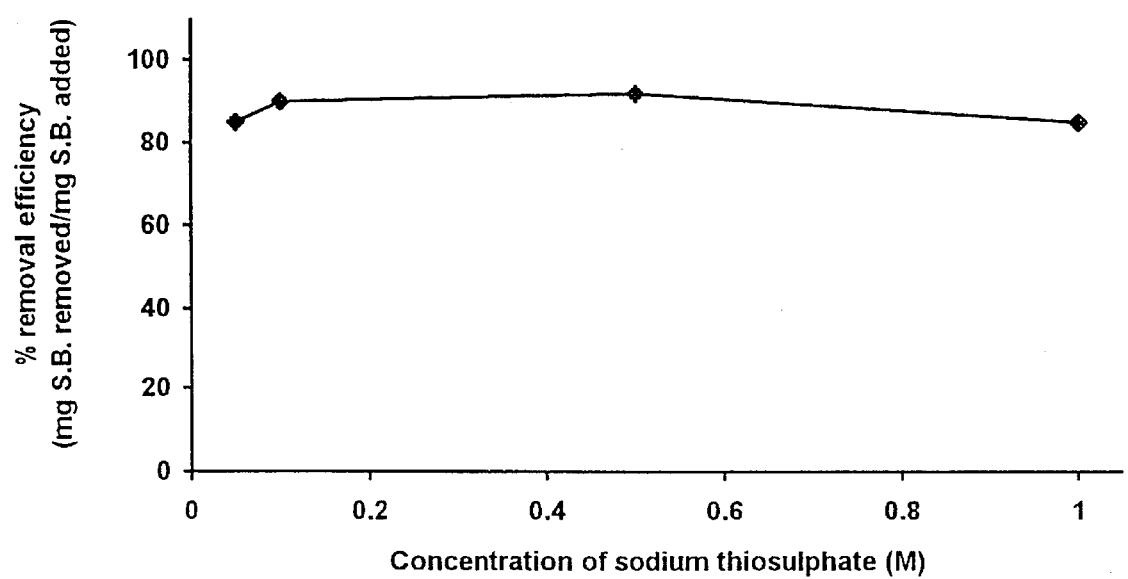
FIG. 6 is a graph of the effect of concentration of sodium thiosulfate on sulphur black dye removal efficiency of resting bacterial cells.

The sulphur black removal efficiency of W3 remained high (about 90%) and was not affected by changes in the concentration of $Na_2S_2O_3$ that ranged from 0.05 to 1.0M. See FIG. 6.

e. Effect of temperature on the sulphur black removal efficiency of W3

10 mg of W3 (in corresponding dry wt.) were resuspended in 2 ml of 0.1M sodium thiosulfate with 0.05 mg/ml of sulphur black. The mixtures were incubated at either 4, 25, 37 or 60° C. for 1 hour. The amount of sulphur black removed by W3 was determined by the standard method of D.2.

Over this range of temperatures, 4° to 60° C., sulphur black removal efficiency of W3 remained at about 85 to 92%.

f. Effect of incubation time on sulphur black removal efficiency of W3

10 mg of W3 (in corresponding dry wt.) were resuspended in 2 ml 0.1M sodium thiosulfate containing 0.05 mg/ml of sulphur black. The resuspension was incubated at room temperature for 1, 30, 60 or 120 minutes. The amount of sulphur black removed by W3 was determined by standard method D.2.

The sulphur black removal efficiency of W3 after 1 minute was slightly lower than the removal efficiency observed after 30 minutes. Similar sulphur black removal efficiencies were observed when the incubation time was extended from 30 to 120 minutes.

g. Effect of pH on sulphur black removal efficiency of W3

Two buffer systems covering pH ranges from 7–13 were used. Buffer system I included phosphate buffer pH 7, tris-(hydroxymethyl)aminomethane buffer pH 9, phosphate-NaOH buffer pH 11 and hydroxide-chloride buffer pH 13. Buffer system II included potassium hydrogen phosphate-NaOH buffer pH 7, glycine-NaHO buffer pH 9, phosphate-NaOH buffer pH 11 and hydroxide-chloride buffer pH 13.

10 mg of W3 (in corresponding dry wt.) was resuspended in 2 ml 0.05M buffer containing 0.1M sodium thiosulfate and 0.05 mg/ml of sulphur black. The resuspension was incubated at room temperature for 1 hour. The amount of sulphur black removed by W3 was determined by the standard method of D.2.

Figure 7:
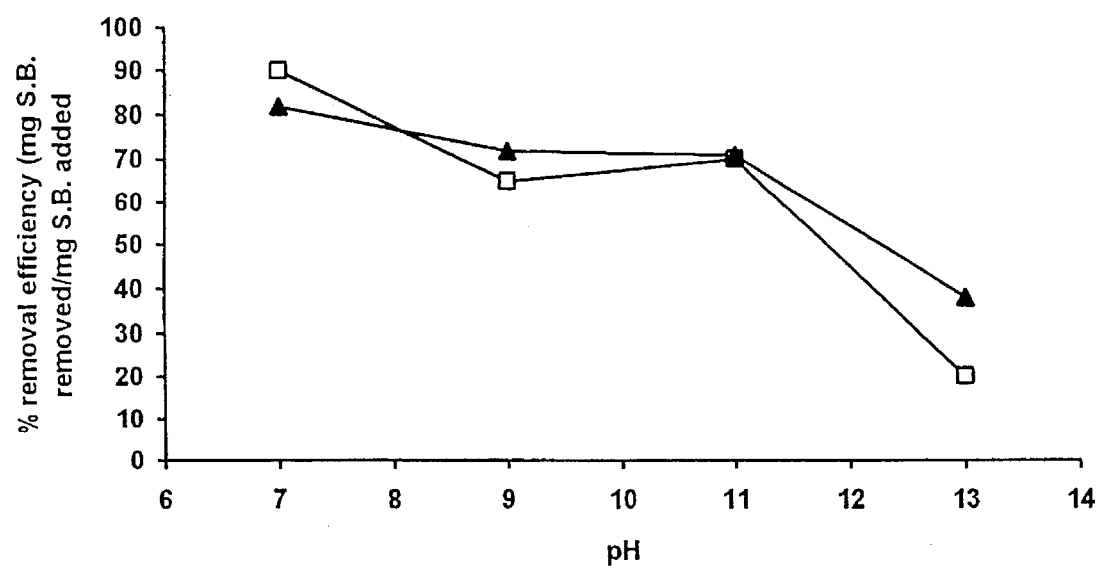
FIG. 7 is a graph of the effect of variations in pH on the sulphur black dye removal efficiency of resting bacterial cells.

The effect of pH was verified by the two buffer systems covering pH 7, 9, 11 and 13. The sulphur black removal efficiency decreased with increasing alkalinity. The sulphur black removal efficiency decreased slightly as the pH increased from 7 to 11, and then decreased dramatically as the pH increased from 11 to 13. See FIG. 7.

h. Effect of different pretreatments on tile sulphur black removal efficiency of W3

10 mg of W3 (in corresponding dry wt.) was exposed to the following chemical or physical pretreatments immediately prior to the sulphur black removal assay. Following pretreatment, the control and the treated samples were harvested by centrifugation at 10,000 rpm for 10 minutes at 4° C. and were washed twice with distilled water. The supernatant were discarded after each centrifugation step. The control and treated cells of W3 were resuspended in 2 ml of 0.1M sodium thiosulfate with 0.05 mg/ml of sulphur black. The resuspensions were incubated at room temperature for 15 minutes. The amount of sulphur black removed by W3 was determined by the standard method D.2. The untreated W3 was used as a control and assigned 100 as relative sulphur black removal efficiency. The relative sulphur black removal efficiency of the various pretreated W3 was about 89 to 102%. The results are found in the table following the descriptions of the various pretreatments that were employed.

Acid treatment—incubate cells in 50 mM HCl at room temperature for 30 minutes or at 100° C. for 10 minutes.

Alkali treatment incubate cells in 50 mM NaOH at room temperature for 30 minutes.

Heat treatment—incubate cells in distilled water at 100° C. for 10 minutes or at 121° C., 15 lb/in² for 20 minutes (i.e. autoclave).

Enzyme tmt.—incubate cells in 0.1 mg/ml of trypsin at 37° C. in neutral pH for 30 minutes.

Ether treatment Resuspend cells in diethyl ether at room temperature for 10 minutes.

Control—Cells were kept in distilled water and stored on ice for 10 or 30 minutes.

TABLE 2

| Treatment | Target component | Relative removal efficiency(%) |
|---|---|---|
| Control | — | 100(assumed) |
| HCl(R.T.) | non-specific | 97.2 |
| HCl(100° C.) | non-specific | 89.4 |
| NaOH | non-specific | 40.4 |
| SDS | non-specific | 101.7 |
| Triton X-100 | non-specific | 99.7 |
| Cetylpyridinium Chloride | non-specific | 99.2 |
| 100° C. | non-specific | 101.5 |
| Autoclave | non-specific | 101.4 |
| Trypsin | protein and peptidoglycan | 97.2 |
| Ether | primarily lipids | 101.2 | i. Removal of sulphur black from the solutions analogous to sulphur black processing solutions comprising sodium thiosulfate 10 mg of W3 (in corresponding dry wt.) were resuspended in a solution having 25% (w/v) sodium thiosulfate (1.0M), 0.1 mg/ml of sulphur black and 5% NaCl (0.86M) in pH 8. The mixture was incubated at room temperature for 30 minutes. The amount of sulphur black removed by W3 was determined by the standard method D.2.

The sulphur black removal efficiency of 10 mg of W3 (in corresponding dry wt.) was about 94% in 2 ml 25% (w/v) sodium thiosulfate (1M), 0.1 mg/ml of sulphur black and 5 (w/v) NaCl (0.86M) at pH 8 after incubation at room temperature for 30 minutes.

j. Complete sulphur black removal from high concentration sulphur black solutions The concentration of sulphur black used in this experiment was 10 times higher than that in standard method D.2. 10 mg of W3 (in corresponding dry wt.) was resuspended in 4 ml of 0.1M sodium thiosulfate solution containing 0.5 mg/ml of sulphur black. The resuspension was incubated at room temperature for 30 minutes. The supernatant was separated from the cells following centrifugation of the resuspension at 10,000 rpm at 4° C. for 10 minutes. The cell pellet was discarded and the supernatant was retained for determination of sulphur black concentration by the standard method of D.2.10 mg of W3 was then added to the supernatant and the procedure was repeated until 99% of the sulphur black was removed.

Figure 8:
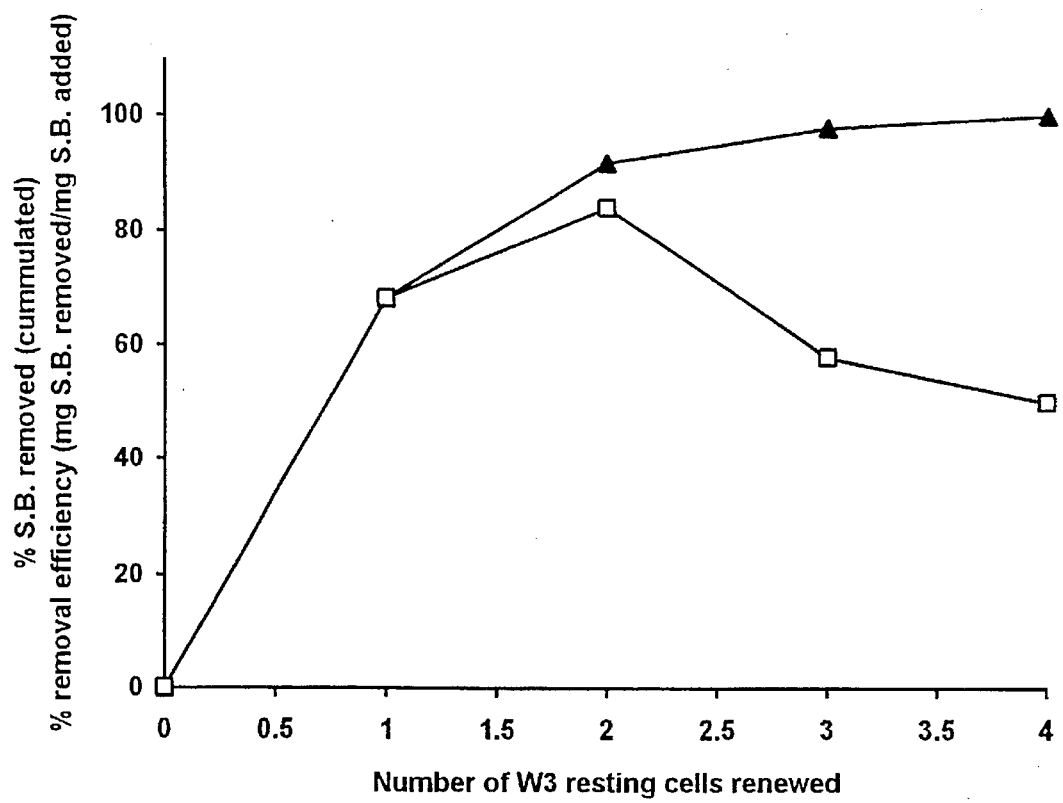
FIG. 8 is a graph showing the removal of sulphur black dye by repeated treatments of the same amount of the bacterial cells.

99% of the sulphur black was removed from 4 ml of a 3.05M sodium thiosulfate solution containing 0.5 mg/ml of sulphur black (the concentration of sulphur black used was 10 times higher than that used in standard method) following four repeated additions of 10 mg of W3 (in corresponding dry wt.). 98% of the sulphur black was removed after 3 repeated additions of cells. However, the sulphur black removal efficiency decreased as the number of renewals of cells, i.e. repeated additions, increased. See FIG. 8.

k. Sulphur-black removal capacity of resting cells of W3

The maximum sulphur black removal capacity of W3 resting cells was evaluated using the following procedure. 10 mg of W3 (in dry wt.) was resuspended in 2 ml of 0.1M sodium thiosulfate with 0.05 mg/ml of sulphur black. The resuspension was incubated at room temperature for 15 minutes. The resuspension was centrifuged at 10,000 rpm for 10 minutes and the concentration of sulphur black left in the supernatant was measure by the standard method of D.2. The supernatant was then discarded. The cell pellet was saved and resuspended in 2 ml of 0.1M sodium thiosulfate with 0.05 mg/ml of sulphur black. The resuspension was then incubated at room temperature for 15 minutes. This procedure was repeated 15 times. The total amount of sulphur black removed by W3 was determined by the standard method of D.2.

It was observed that 10 mg of W3 (in corresponding dry wt.) removed 0.5 mg of sulphur black if 2 ml 0.1M sodium thiosulfate with 0.05 mg/ml of sulphur black was renewed 15 times. Since the saturation of sulphur black adsorption had not yet been reached, it was expected that the maximum sulphur black removal capacity of 10 mg W3 should be higher than 0.05 (mg sulphur black removed/mg cells added).

l. Effect of W3 treatment on the concentration of sodium thiosulfate 10 mg of W3 (in corresponding dry wt.) was resuspended in 2 ml of 0.05M sodium thiosulfate with and without 0.05 mg/ml of sulphur black at room temperature for 15 minutes. The initial and final concentration of sodium thiosulfate was determined by the following formula:

$$\text{Mole of } I_2 \text{ used} = \text{Vol. of } I_2 \text{ used} \times \text{molarity of } I_2$$
$$= 2 \times \text{Vol. of } Na_2S_2O_3 \text{ used} \times \text{molarity of } Na_2S_2O_3$$

$$\text{Molarity of } Na_2S_2O_3 = \frac{\text{Vol. of } I_2 \text{ used} \times \text{molarity of } I_2}{2 \times \text{Vol. of } Na_2S_2O_3 \text{ used}}$$

No change was observed in the concentration of either sodium thiosulfate solution after W3 treatment for 30 minutes at room temperature.

m. Adsorption of sulphur black by dead W3 cells

The amount of sulphur black adsorbed is not affected by killing the W3, regardless of how the cells are killed, e.g. by heating, acid, or detergents. It was therefore concluded that sulphur black binding by W3 cells is independent of respiration or other cell metabolic activity. In repeated bioadsorption studies, it was consistently found that the sulphur black binding efficiency of W3 was not influenced by killing the cells.

n. Active agents on the cell surface for sulphur black binding.

Sodium dodecyl sulfate (an artionic denaturing surfactant), Triton X-100 (a nonionic nondenaturing surfactant) and cetylpyridinium chloride (a cationic denaturing surfactant) had neither a positive nor a negative effect on sulphur black binding by W3.

o. Effect of sodium thiosulfate on sulphur black binding.

The presence of $Na_2S_2O_3$ is relevant to sulphur black binding because the sulphur black removal efficiency was reduced in the absence of $Na_2S_2O_3$. However, a similar amount of sulphur black was adsorbed by W3 in the presence of $Na_2S_2O_3$ in the range of 0.05 to 1.0M. This suggests that a minimal concentration of $Na_2S_2O_3$ (±0.05M) is desirable to maintain the high sulphur black binding efficiency of W3.

II. Isolation and Characterization of the Activity of the Biodegradation Strain L5

A. Isolation of L5

Polluted water samples were collected from the South China region. Bacterial strains capable of degrading sulphur black were isolated from these samples by inoculating 100 ml IM liquid aliquots comprising sulphur black with inoculate from the polluted water samples. Aliquots which displayed a color change subsequent to inoculation were deemed to comprise biodegradation bacterial strains.

The isolation of biodegradation strains, as opposed to bioadsorption strains, was confirmed by using the following procedure. 20–30 ml of IM agar was poured onto a petri plate and allowed to solidify for one day. 5 ml of IM agar was combined with bacterial and sulphur black dye at 6% final dilution. This second agar solution was poured onto the surface of the solidified agar on the petri plate. The second layer was allowed to solidify. The petri plate was incubated at 37° C. for one day. A significant color change was observed indicating that the bacteria present in the top agar layer was L5.

B. Characterization of L5

1. Haloforming ability

To determine whether the enzymes responsible for the sulphur black degradation activity of L5 are present within the cells or on the surface of the cells, the halo forming test was employed. A sulphur black IM plate was spotted with an L5 culture. The plate was incubated at 37° C. for one week. Following incubation, no clear halo in the otherwise black color of the plate was observed. It was concluded that either adsorption or absorption was necessary for biodegradation of sulphur black by L5. In other words, the biodegradation enzyme was not secreted by the L5 into the ambient medium.

2. Effect of sulphur black on the growth of curve of L5

Figure 9:
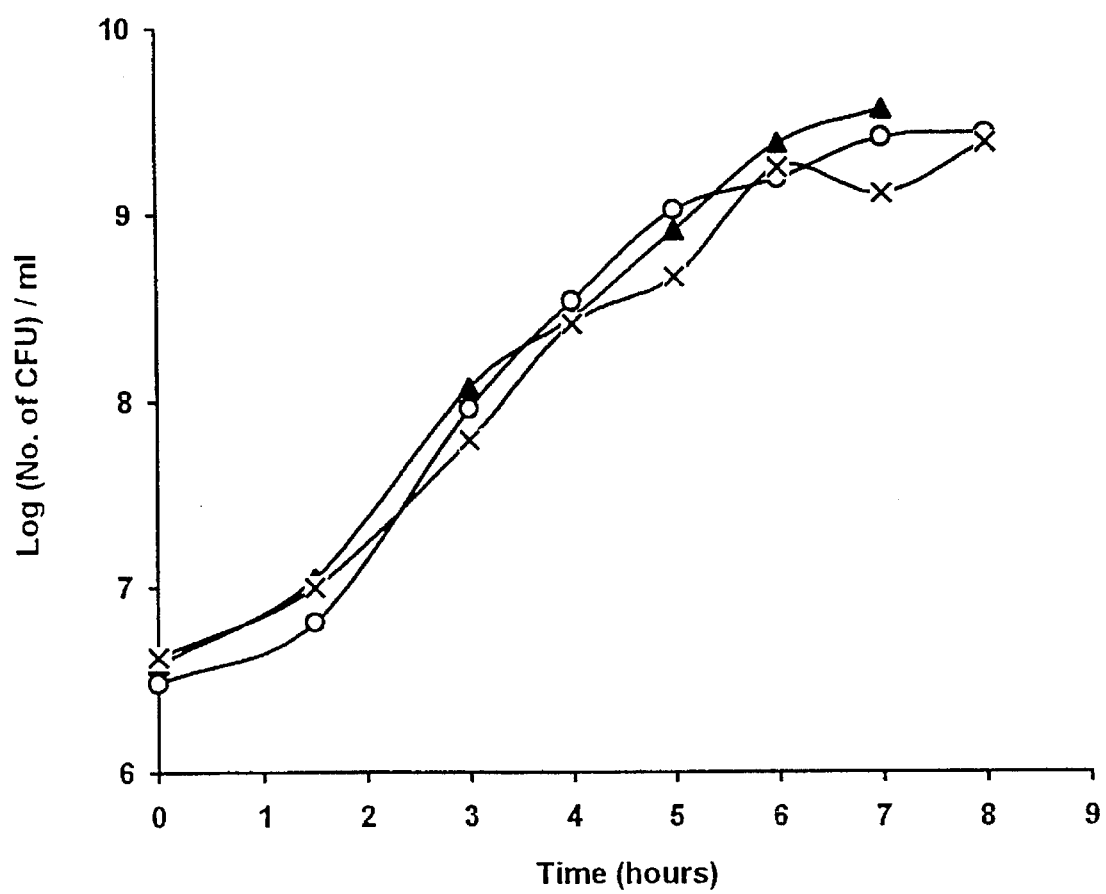
FIG. 9 is a graph representing the growth curve of L5.

It was observed that the presence or absence of sulphur black in the ambient medium of the L5 had no effect on the growth curve of L5. See FIG. 9.

3. Additional characterizations of L5

Using conventional methods, these additional characterizations of the L5 strain were made.

a) L5 is a gram positive cocci;

b) L5 is facultatively anaerobic;

c) L5 does not possess oxidase activity;

d) L5 ferments glucose, arabinose and xylose to produce acid and gas;

e) L5 ferments lactose, maltose, sucrose and mannitol to produce gas;

f) L5 possesses catalase activity;

g) L5 displays positive IMV C activity;

h) L5 produced hydrogen sulphide from sulphate;

i) L5 hydrolyzes starch, tributyrin and casein but does not hydrolyze gelatin;

j) L5 reduces litmus;

k) L5 possesses both rennin and pepsin like enzymes; and l) L5 displays resistance to the following antibiotics: ampicillin, bacitracin, neomycin, penicillin G, polymyxin B, rifampin, streptotnycin, tetracycline, oxytetracycline, as well as intermediate resistance to nalidixic acid.

The subject method and microorganisms may be used for treating a wide variety of composites through either bioadsorption or biodegradation. Bioadsorption may find particular use in the treatment of waste streams, such as the thiosulfate waste stream resulting from the production of sulphur black dye. Bioadsorption may also be used for other waste streams, particularly associated with the dying of textile. The method may comprise one or more stages. As already indicated, the cells can be grown and killed and used for adsorption. This may be particularly useful, where one wishes to reduce the concentration level of the sulphur black dye, prior to using viable cells to both adsorb and degrade the sulphur black dye. By reducing the amount of sulphur black dye present in the waste stream one may reduce the time for the processing of the resulting stream by viable cells.

Biodegradation provides further methods for treatment of compositions in which sulphur black dye is a contaminant. In some instances, it may be useful to transform the subject cells to provide for capabilities for degradation of other waste materials which may be present in the common waste stream. Thus, the subject hosts may be modified to provide for multiple capacities. Alternatively, the gene obtained as described above may be used to transform other hosts which may be more convenient as to growth properties, harvesting, safety or the like. In this manner, different bacterial organisms may be employed for one or more purposes.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated bacterium capable of reducing the concentration of sulphur black dye in a substrate, wherein said reducing is accomplished by biadsorption of said sulphur black dye by said bacterium, wherein said bacterium is designated W3 and has an ATCC number of 55566.

2. An isolated bacterium capable of reducing the concentration of sulphur black dye in a substrate, wherein said reducing is accomplished by biodegradation of said sulphur black dye by said bacterium, wherein said bacterium is aerobic and faculatively anaerobic and is designated L5 and has an ATCC number of 55565.

* * * * *

UNITED STATES PATENT AND TRADEMARK OFFICE
CERTIFICATE OF CORRECTION

PATENT NO.    : 5,610,064
DATED         : March 11, 1997
INVENTOR(S)   : Kai Keung Mark Page 1 of 1

It is certified that error appears in the above-identified patent and that said Letters Patent is hereby corrected as shown below:

<u>Title page,</u>
Item [75], Inventor, "Mark K. Keung" should read -- Kai Keung Mark --.

Signed and Sealed this

Second Day of May, 2006

JON W. DUDAS
*Director of the United States Patent and Trademark Office*